United States Patent [19]

Peiffer

[11] Patent Number: 5,026,382
[45] Date of Patent: Jun. 25, 1991

[54] HEMOSTATIC CLIP

[75] Inventor: James E. Peiffer, Evergreen, Colo.

[73] Assignee: Horizon Surgical, Inc., Evergreen, Colo.

[21] Appl. No.: 573,359

[22] Filed: Aug. 27, 1990

[51] Int. Cl.$^5$ .............................................. A61B 17/00
[52] U.S. Cl. ..................................... 606/158; 606/157
[58] Field of Search .................. 606/157, 158; 227/901

[56] References Cited

U.S. PATENT DOCUMENTS

| 3,363,628 | 1/1968 | Wood | 606/158 |
| 4,702,247 | 10/1987 | Blake, III et al. | 606/157 |
| 4,799,481 | 1/1989 | Transue et al. | 606/158 |
| 4,844,066 | 7/1989 | Stein | 606/158 |
| 4,976,722 | 12/1990 | Failla | 606/158 |
| 4,979,950 | 12/1990 | Transue et al. | 606/158 |

Primary Examiner—Stephen C. Pellegrino
Assistant Examiner—Gary Jackson
Attorney, Agent, or Firm—James R. Young

[57] ABSTRACT

Disclosed is a hemostatic clip formed into a horseshoe shape from material having a generally triangular cross-section. The mating edges of the clip contain a groove used to provide space for the walls of the vessel when the clip is applied. The groove is located approximately in the center of the mating surfaces, and its width is less than one third the width of the mating surfaces. Because the width is less than one third of the mating surfaces, the other two thirds of the mating surfaces are too wide to fit into the groove, should the clip be applied in a misaligned manner. A plurality of slots in the occlusive surface of the clip help to hold the clip in position on a vessel, once the clip has been clamped into place. After the slots have been placed into the clip, the clip is processed in a tumbling operation to remove any serrations around the slots or at any other place on the clip. Thus, no protrusions remain around the slots to puncture a vessel during ligation. The triangular shape of the clip allows the clip to better fit into the jaws of the applier.

11 Claims, 3 Drawing Sheets

HEMOSTATIC CLIP

BACKGROUND OF THE INVENTION

This invention relates to surgical equipment, and more particularly to equipment used to clamp blood vessels. Even more particularly, the invention relates to hemostatic clips used to ligate or clamp blood vessels during surgical procedures.

Hemostatic clips have been used in surgery for over 60 years. They were designed to perform two basic functions—ligation of a vessel, nerve, or fluid duct in the human body; or marking a specific surgical site, typically the periphery of a tumor, which will later show up on an X-ray. The clips are permanently implanted in the body and are radiopaque. Originally hemostatic clips were formed in a "V" shape. However, when this shape is closed, it tends to push the vessel away from the clip or cut the vessel rather than clamp it. This problem was solved by a preformed hemostatic clip which resembles the shape of a horseshoe, described in U.S. Pat. Nos. 3,323,216 and 3,363,628, which is now commonly used. The horseshoe clip has two essentially parallel legs which cause an initial distal tip to tip closing action that contains the vessel within the clip to fully control the vessel before ligation.

Occasionally the clip of U.S. Pat. No. 3,363,628 will sever a vessel or the clip will slip from the point of application. As will be described below, if the prior art clips are applied with a misaligned applier, no space will be left between the arms of the clip for the walls of the vessel, and the vessel will be crushed. An inadequate vessel wall surface contact area may also cause the clip to slip from its point of application.

This problem is well known in the art, and others have attempted to solve it. For example, U.S. Pat. No. 4,188,953 issued Feb. 19, 1980 to Klieman, et al. placed diagonal recesses in the two arms. U.S. Pat. No. 4,844,066 issued July 4, 1989 to Stein left an ungrooved area at the tip of the clip.

The manufacturing process for prior art clips often leaves rough surfaces on the clip and may leave "sharks teeth" where the lateral serrations were stamped. These may gouge the vessel when the clip is applied.

It is thus apparent that there is a need in the art for an improved hemostatic clip that will leave space for the vessel walls, even if applied by a misaligned applier. There is a further need for a clip with a large, smooth surface area free from sharp edges and protrusions. The present invention meets these needs.

SUMMARY OF THE INVENTION

It is an object of the present invention to provide an improved system hemostatic clip for ligating vessels in the human body.

It is another object of the invention to provide such a clip that leaves space for the vessel walls, even if the clip is applied with a misaligned applier.

Another object of the invention is to provide such a clip having a triangular shape to better fit into the jaws of a clip applier.

A further object of the invention is to provide a clip having a smooth surface lacking in sharp, "sharks teeth" protrusions on the edges of the clip.

A still further object of the invention is increased vessel wall contact area.

The above and other objects of the invention are accomplished in a hemostatic clip formed from material having a generally triangular cross-sectional shape, which is formed into a horseshoe-shaped clip. The mating edges of the clip contain a groove used to provide space for the walls of the vessel when the clip is fully closed. The groove is located approximately in the center of the mating surfaces, and its width is less than one third the width of the mating surfaces. Because the width is less than one third of the mating surfaces, the other two thirds of the mating surfaces are too wide to fit into the groove, should the clip be applied in a misaligned manner.

A plurality of slots in the occlusive surface of the clip help to hold the clip in position on a vessel, once the clip has been clamped into place. During manufacture the lateral slots are stamped into the clip. The clip is then processed in a tumbling operation to remove all sharp edges around the slots or at any other place on the clip. Thus, no protrusions remain on any surface of the clip to gouge a vessel during ligation.

The triangular shape of the clip allows the clip to better fit into the jaws of a conventional and widely used applier.

BRIEF DESCRIPTION OF THE DRAWINGS

The above and other objects, features, and advantages of the invention will be better understood by reading the following more particular description of the invention, presented in conjunction with the following drawings, wherein.

DESCRIPTION OF THE PREFERRED EMBODIMENT

The following description is of the best presently contemplated mode of carrying out the present invention. This description is not to be taken in a limiting sense but is made merely for the purpose of describing the general principles of the invention. The scope of the invention should be determined by referencing the appended claims.

Figure 1:
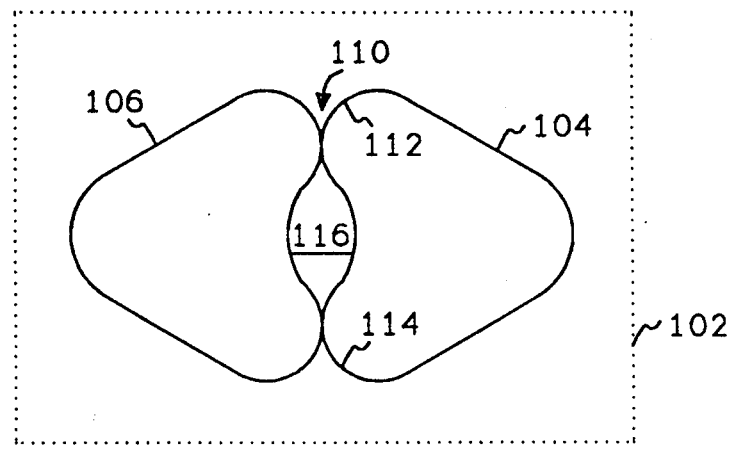
FIG. 1 shows a plan view of the end of a prior art hemostatic clip.

FIG. 1 shows a plan view of the end of a prior art hemostatic clip. Referring now to FIG. 1, a clip 102 has legs 104 and 106 which mate to form an occlusive surface 110. Vessel contact surface areas 112 and 114 contact similar areas on the opposite leg 106 of the clip 102 while leaving a gap 116 for the walls of the vessel being clamped.

Figure 2:
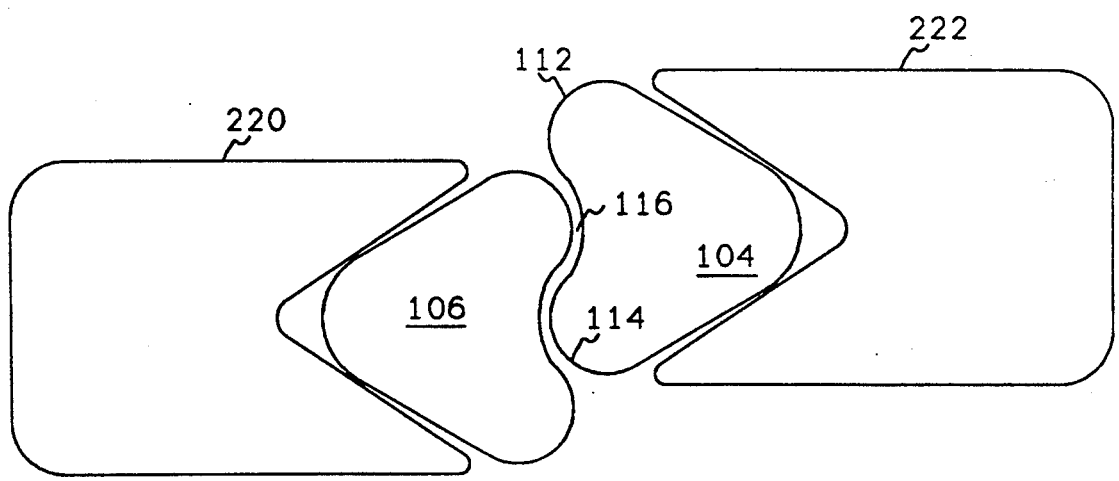
FIG. 2 shows a plan view of the end of a prior art hemostatic clip after such clip has been applied with a misaligned applier.

FIG. 2 shows a plan view of the end of a prior art hemostatic clip after such clip has been applied with a misaligned applier. Referring now to FIG. 2, the legs 104 and 106 of the clip have been clamped together in a misaligned fashion, which can occur when the jaws 220, 222 of the clip applier are misaligned. Because of the misalignment, the vessel contact surface area 114 has been forced into the gap 116, thus leaving no space for the walls of the vessel. The lack of a gap to contain the vessels walls causes a severe degradation in the performance of the clip, and will cause the blood vessel to be crushed and possibly severed.

Figure 3:
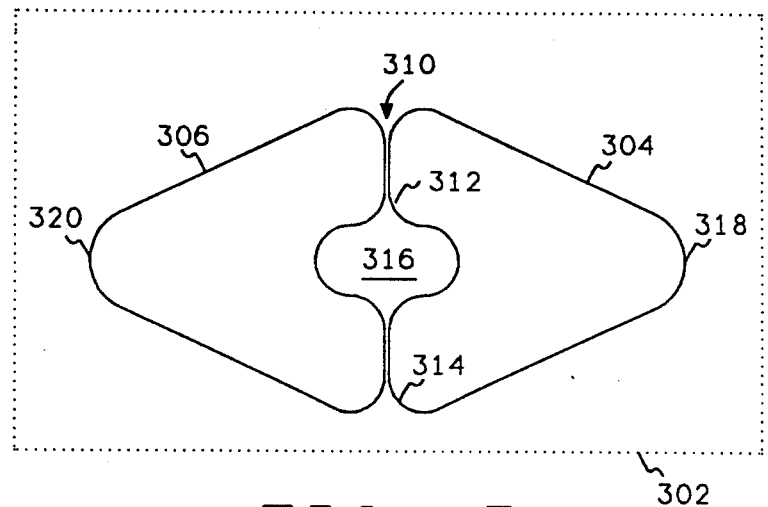
FIG. 3 shows a plan view of the end of the clip of the present invention.

FIG. 3 shows a plan view of the end of the clip of the present invention. Referring now to FIG. 3, a clip 302 has legs 304 and 306 which mate to form an occlusive surface 310. Vessel contact surface areas 312 and 314 contact similar areas on the opposite leg 306 of the clip 302 while leaving a gap 316 for the walls of the vessel being clamped. The groove that forms the gap 316 is less than one third the width of the occlusive surface 310. Increased vessel contact surface area, combined with a large vessel area displacement gap, insures that the clip will not slip from the point of application.

Figure 4:
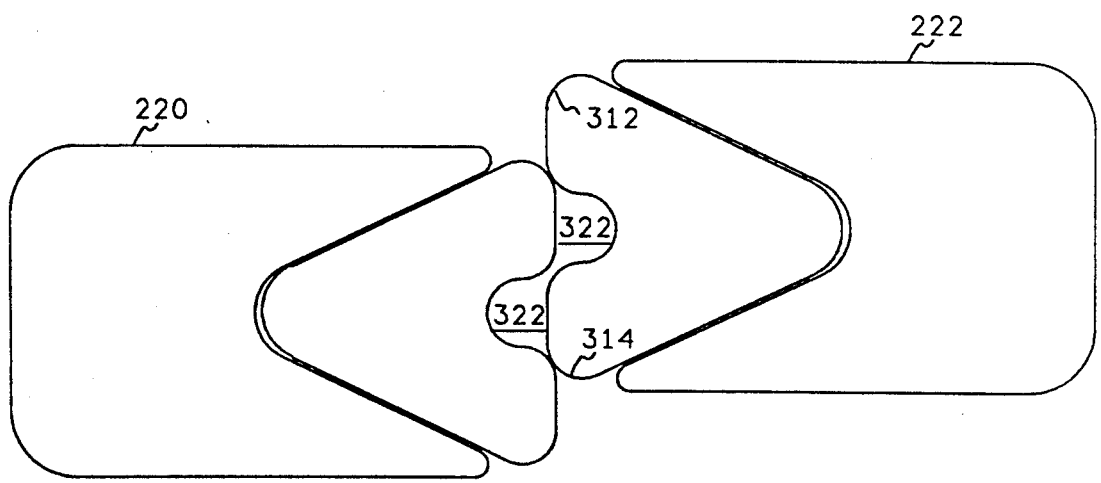
FIG. 4 shows a plan view of the end of the clip of the present invention after such clip has been applied with a misaligned applier.

FIG. 4 shows a plan view of the end of the clip of the present invention after such clip has been applied with a misaligned applier. Referring now to FIG. 4, the legs 304 and 306 of the clip 302 have been pressed together by an applier with misaligned jaws 220, 222. Because of the misalignment, the vessel contact surface area 314 fits across part of the gap 316. However, unlike prior art clips, the vessel contact surface area 314 is wider than the groove which forms the gap 316, therefore the vessel contact surface area 314 will not fit into the gap 322. Because of this, the gap 322 remains between the legs 304 and 306 of the clip 302, thus providing room for the walls of the vessel being clamped. Even though the shape of the gap 322 is different from the shape of the groove 316 in a properly aligned clip, nonetheless a gap is left which significantly reduces the likelihood of crushing or severing the vessel.

Another important feature of the clip of the present invention, is the triangular shape. Because of this triangular shape, the edges 318 and 320 will more easily fit into the grooves of the commonly used clip applier, thus increasing the likelihood of correct alignment and proper clip closure.

Figure 5:
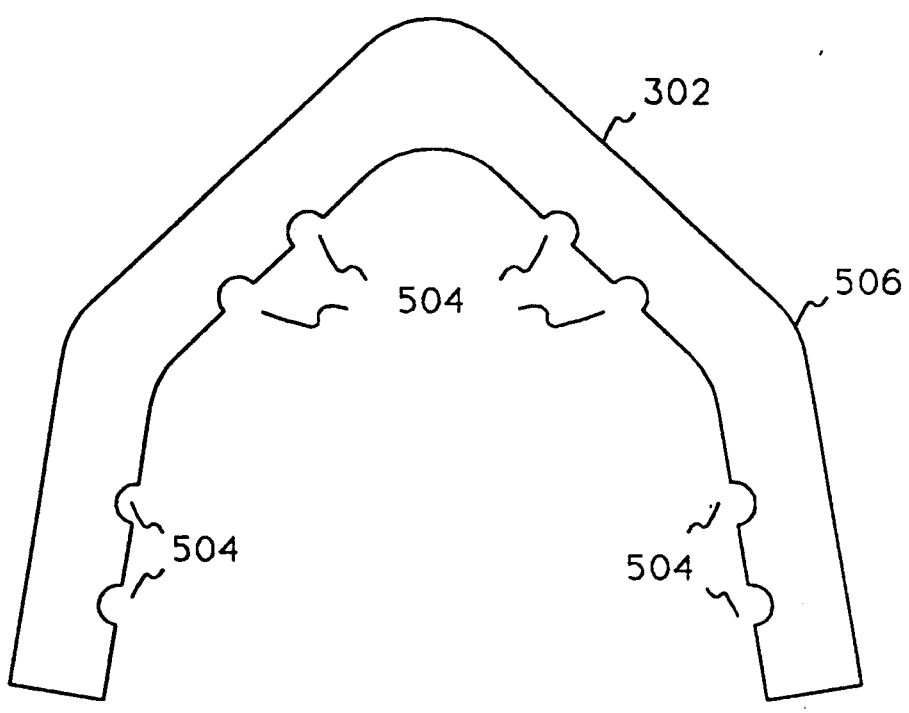
FIG. 5 shows a side view of the clip of the present invention.

FIG. 5 shows a side view of the clip of the present invention. Referring now to FIG. 5, the clip 302 is formed into a horseshoe shape by making a bend at location 506. Serrations 504 are placed in the clip to provide a lateral vessel wall displacement area. In prior art clips, when the serrations 504 are formed, material may be forced away from the clip and leave small protrusions which form "shark's teeth" that may cause the clip to gouge a vessel being clamped. In the clip of the present invention, after forming the serrations 504, the clip is processed in a tumbling operation to remove all the small shark's teeth protrusions. Thus, the clip of the present invention is much less likely to gouge a vessel being ligated.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the spirit and scope of the present invention. The disclosures and the description herein are intended to be illustrative and are not in any sense limiting of the invention, more preferably defined in scope by the following claims.

What is claimed is:

1. A hemostatic clip comprising:
    a pair of arms formed from a single elongated strip of deformable material, said arms being interconnected at one end and open at the other end and arranged in laterally spaced apart substantially parallel relation, each of said arms being substantially triangular in cross-section with a flat side facing inwardly and with the apex facing outwardly;
    a longitudinal groove formed along said flat side of said arms, said groove having a width less than one third the width of said flat side, and said groove being formed substantially in the center of said flat side.

2. The hemostatic clip of claim 1 further comprising at least one crosswise serration in said flat side of one of said arms.

3. The hemostatic clip of claim 1 wherein said strip is formed of a surgical metal.

4. The hemostatic clip of claim 1 wherein said strip is formed of a material slowly absorbable in body fluids.

5. The hemostatic clip of claim 1 wherein said strip is formed of a non-metallic sterile material.

6. A process for making a hemostatic clip comprising the steps of:
    (a) forming a pair of arms from a single elongated substantially triangular strip of deformable material, said arms being formed to interconnect at one end and to be open at the other end, formed to be arranged in laterally spaced apart substantially parallel relation, and formed having a flat side facing inwardly with the apex of said substantially triangular strip facing outwardly;
    (b) shaping a longitudinal groove along said flat side of said arms, said groove being shaped to a width less than one third the width of said flat side, and said groove being located substantially in the center of said flat side.

7. The process of claim 6 further comprising the step of:
    (c) creating at least one crosswise serration in said flat side of one of said arms.

8. The process of claim 7 further comprising the step of:
    (d) removing any sharp protrusions created during steps (b) or (c).

9. The process of claim 8 wherein step (d) further comprises the step of:
    (d1) tumbling said clips;
    whereby any sharp protrusions created during steps (b) or (c) are removed.

10. The process of claim 6 further comprising the step of:
    (d) removing any sharp protrusions created during step (b).

11. The process of claim 10 wherein step (d) further comprises the step of:
    (d1) tumbling said clips;
    whereby any sharp protrusions created during step (b).

* * * * *